United States Patent [19]

Anderson et al.

[11] 4,136,690

[45] Jan. 30, 1979

[54] METHOD AND APPARATUS FOR VECTOR ANALYSIS OF ECG ARRHYTHMIAS

[75] Inventors: Donald L. Anderson, Huntington Beach; Isaac R. Cherry, Mission Viejo, both of Calif.

[73] Assignee: Del Mar Avionics, Irvine, Calif.

[21] Appl. No.: 847,400

[22] Filed: Oct. 31, 1977

[51] Int. Cl.² .............................................. A61B 5/04
[52] U.S. Cl. .............................................. 128/2.06 A
[58] Field of Search ..................... 128/2.06 A, 2.06 R, 128/2.06 V; 364/417

[56] References Cited

U.S. PATENT DOCUMENTS

| | | | |
|---|---|---|---|
| 3,548,813 | 12/1972 | Berner | 128/2.06 V |
| 3,554,187 | 1/1972 | Glassner | 128/2.06 A |
| 3,572,321 | 3/1971 | Bloomfield | 128/2.06 A |
| 3,861,387 | 1/1975 | Lawhorn et al. | 128/2.06 A |
| 3,939,824 | 2/1976 | Arneson et al. | 128/2.06 A |

OTHER PUBLICATIONS

Silcocks et al., "Proceedings of the 7th Annual Biomedical Sciences Instrumentation Symposium on Imagery in Medicine," Ann Arbor, Michigan, May 19–22, 1969, pp. 37–43.
Bourne, "Medical & Biological Engineering", vol. 12, No. 6, Nov. 1974, pp. 859–863.

Primary Examiner—William E. Kamm
Attorney, Agent, or Firm—Smyth, Pavitt, Siegemund, Jones & Martella

[57] ABSTRACT

ECG signals from two approximately orthogonal leads are combined in a rectangular-to-polar coordinate converter to obtain signals representing the magnitude and angle of the vector. The vector angle existing at the instant the magnitude of the QRS vector reaches its peak is first identified, and a voltage corresponding to the vector angle is sampled and stored for later use. Secondly, the vector angle existing at the instant the magnitude of the T-wave vector reaches its peak later in the cardiac cycle, is identified, and a voltage corresponding to this second vector angle is sampled and stored. The voltages representing the QRS and the T-wave vector angles are then applied to a differential amplifier to obtain a difference voltage representing the angular difference existing between the two maximal vectors. This angular difference possesses certain characteristics which are diagnostically significant. A classifying circuit determines which one of a number of angular ranges the angular difference falls into. A counter is provided for each angular range to accumulate over successive heartbeats the number of differences which have fallen into each of the angular ranges, and the cumulative counts are displayed.

22 Claims, 5 Drawing Figures

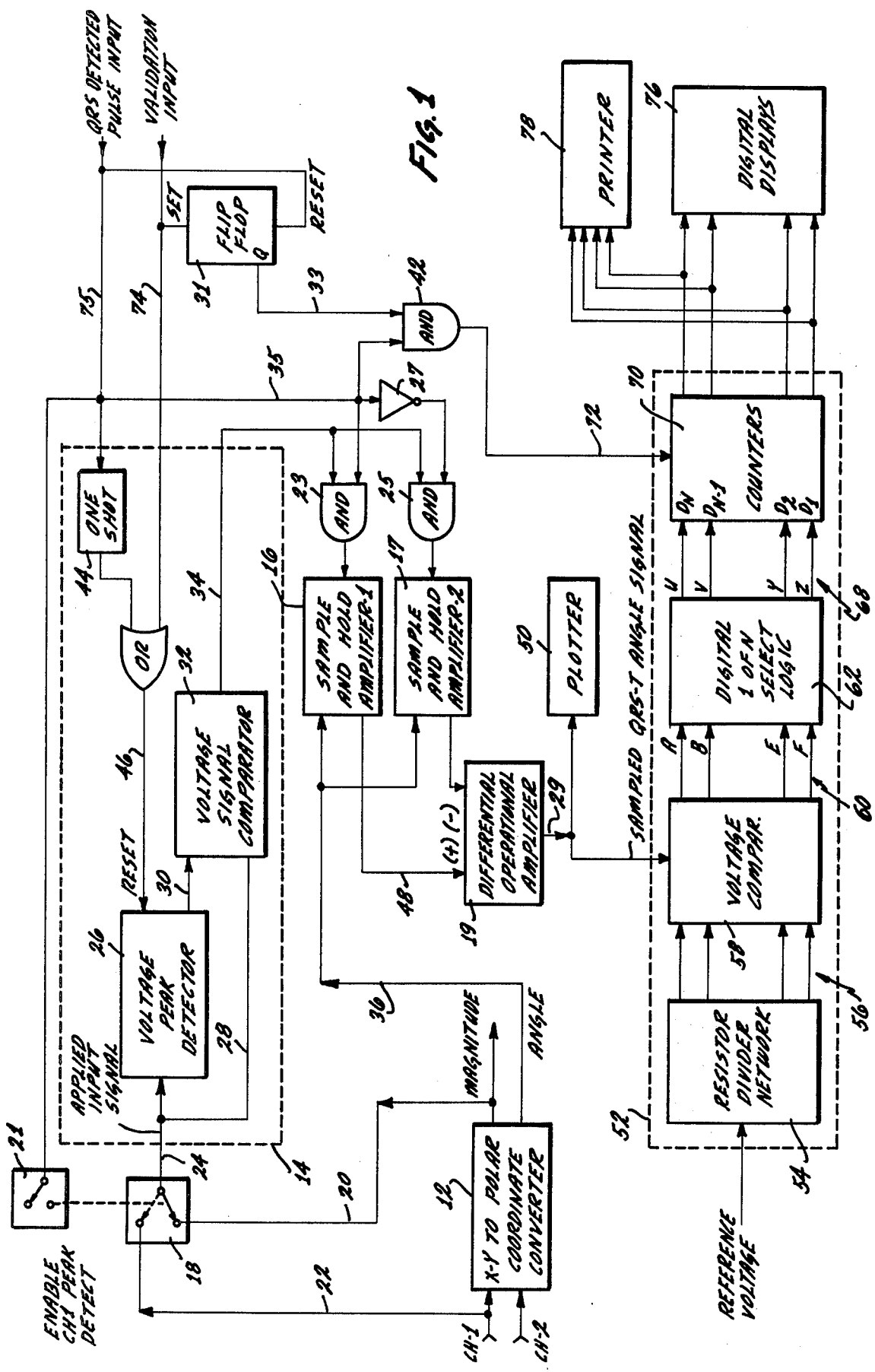

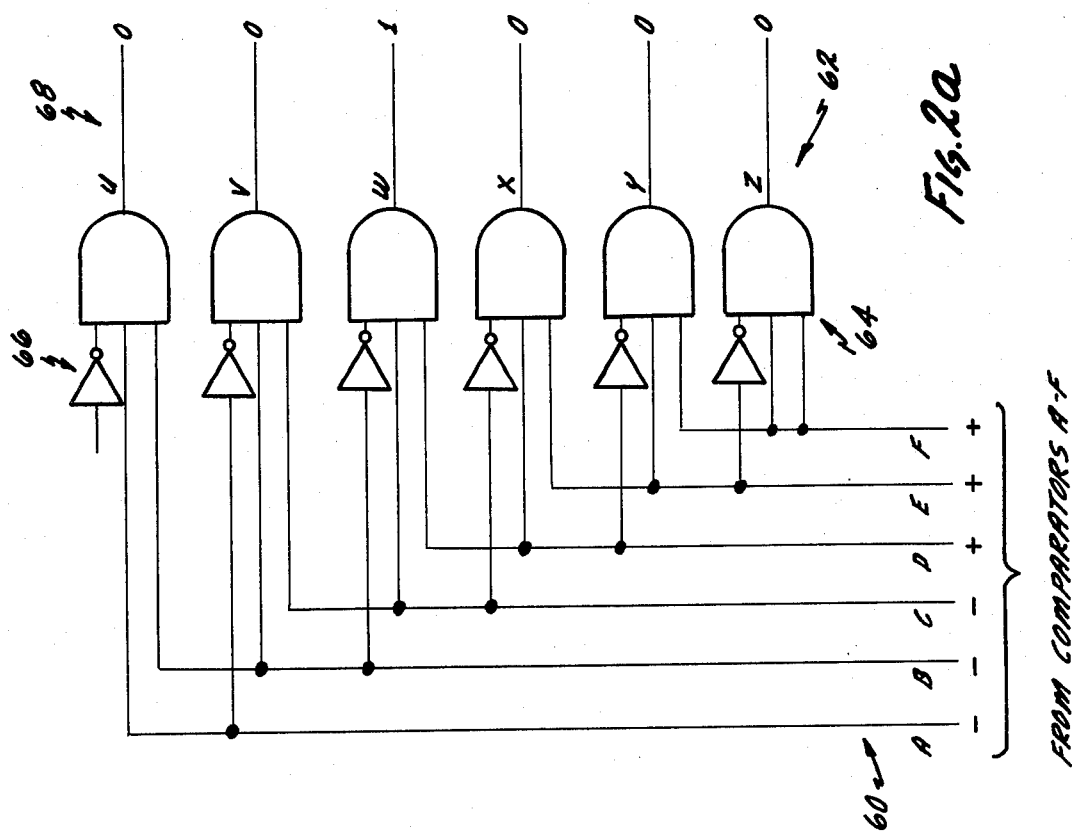

METHOD AND APPARATUS FOR VECTOR ANALYSIS OF ECG ARRHYTHMIAS

BACKGROUND OF THE INVENTION

1. Field of the Invention

The present invention is in the field of medical electronics and specifically relates to apparatus and method for the detection, definition and classification of ectopic heartbeats using two-channel vector ECG signals.

2. The Prior Art

It has long been known that medically-significant vector electrocardiograms can be produced through the use of a three-lead system. Previous studies have already indicated merit in the vector cardiographic analysis of anomalous and ectopic beats for identifying the site of origin of ectopic beats. Such anomalous beats not only commonly result in alteration of readily apparent direction and magnitude of QRS and T force vectors, but also affect the direction of rotation QRS vector forces, often accompanied by abnormal delays of QRS vector inscription. The latter characteristics are not readily apparent in analog electrocardiographic signals, and thus the vectorcardiogram gives additional discriminative data. The adjunctive vectorcardiographic data complements the analog cardiographic signal data by providing a visual integrated picture of the electrical activity.

The preponderance of the diagnostic vector electrocardiographic studies have been carried out using the Frank lead system or a modified McFee lead system, which lead systems were designed to measure horizontal, longitudinal and saggital plane forces.

In U.S. Pat. application Ser. No. 786,252, filed Apr. 11, 1977 for VECTORCARDIOGRAPHIC METHOD FOR AMBULATORY PATIENTS, Dr. Harold L. Kennedy discloses a method for obtaining vectorcardiographs using a two-lead system. This simplified lead system using the $V_1$ and $V_5$ electrode sites was developed specifically to facilitate diagnosis and identification of cardiac dysrhythmias, particularly anomalous extrasystols, as seen in the lead $V_1$, and to best detect left ventricular myocardial ischemia by employing a commonly used exercise-sensitive lead, chest bipolar lead $V_5$.

The simplified two-lead system disclosed in the Kennedy application identified above has proven to be medically useful for producing vectorcardiograms for the diagnosis of arrhythmias, and consequently, with the widening use of the method, increasing amounts of two-channel vectorcardiographic signals can be expected to be produced. Increasing amounts of time and manpower will be devoted to the analysis of such data, and the need for apparatus for automatically analyzing the data has become clear.

SUMMARY OF THE INVENTION

The present invention is a first step towards automating the analysis of two-channel vectorcardiographic data. Because vector data lends itself to many different types of analysis, it is recognized that different types of circuits will be required to implement the various types of analyses to be performed.

The present application discloses apparatus and method for improved ECG arrhythmia detection utilizing information from two-channel signals. Although this apparatus can, in a particular case, use two of the three channels normally employed for vector cardiography, it is particularly suited, but not limited, to the high-speed analysis of long-term, two-channel ECG magnetic tape recordings (commonly referred to as Holter recordings) of ambulatory and bed-ridden subjects.

In vector cardiography, the tip of the vector which represents the electrocardial potentials typically traces an oval or cardioid trajectory during the course of each ventricular depolarization. Previous clinical studies, using data from three-lead vector cardiograph systems, have indicated the diagnostic value of the maximal QRS and T vectors which are the vectors drawn from the starting point of the loop to the farthest points of the QRS and T loops. The apparatus of the present invention permits measurement and analysis of these maximal vectors.

The maximal vector should not be confused with the mean direction which is the vector equal to the sum of all of the instantaneous vectors. The present invention includes apparatus for measuring the angle between the QRS peak vector and the T-wave peak vector. The apparatus can also be used to measure either of these peak vectors separately.

The absolute values of the QRS peak vector, the T-wave peak vector, and their difference are not of prime importance for diagnostic purposes, since the absolute values vary from patient to patient as well as with variations in the positioning of the electrodes on the patient. Instead, in each instance, it is departures from the angles normally observed in a given patient that are diagnostically significant.

The scalar representation of an abnormal supraventricular complex, particularly if nodal-originating, may appear as a bizarre waveform closely resembling a ventricular-originating arrhythmia. However, the relationship between the depolarization potentials represented by the QRS vector forces and the repolarization potential represented by the T vector forces has been proven to be nearly identical for all supraventricular originating complexes, both normal and abnormal. As a result of this fact, a first condition that can be distinguished is whether the ectopic complex is truly of supraventricular origin, the categorization of which includes the normal pacemaker (S-A node) complexes in addition to abnormal atrial and nodal ectopic beats. Thus, it is of utmost importance and utility that the differential vector angle can initially aid in the diagnoses and categorization of supraventricular ectopics, whereas a single (scalar) lead system cannot reliably be used to do so.

Additionally, ventricular ectopic complexes of significantly different points of origin (foci) within the ventricles also display significantly different vector angles. Therefore, further categories can be set up for the purpose of identifying the relative foci of the ectopic events, and to some extent (when the lead configuration and heart position are known), the location of the foci within the heart muscle itself.

Ventricular ectopi rarely originate from more than five significantly separate foci, and typically originate from one to three foci. Therefore, considerable simplification can ultimately be achieved in the overall circuit mechanization.

In the present invention, two-channel, approximately orthogonal ECG signals are applied to a rectangular-to-polar coordinate converter, which produces two output signals showing respectively the instantaneous magnitude and angle of the vector. In the present invention, not all of the instantaneous values of the vector angles are of interest, but primarily the vector angles at the instants when the ventricular depolarization (QRS) and repolarization (T) complexes reach their peaks. These angles are then subtracted to determine the angular difference between the QRS and T vectors which henceforth will be termed "QRS-T angle" or "QRS-T vector angle".

The first vector measurement is performed on the QRS complex, since it occurs first, is the most predominant and is always present, regardless of the ectopic origin. In one embodiment, this QRS angle is determined as the instant when the magnitude of the QRS vector reaches its maximum value. It is recognized, however, that if the loop traced by the tip of the vector is nearly circular, it will be difficult to determine with precision the instant at which the maximum magnitude of the vector is reached. When loops of this kind are encountered, it is convenient to switch to a different mode of operation in which the apex of the ventricular complex is determined from one of the channels of ECG signals as being the instant when the R peak occurs.

In either event, when the QRS peak has been detected, the instantaneous value of the vector angle is sensed by a first sample-and-hold amplifier which temporarily stores the sensed value of QRS angle.

After each QRS angle has been measured, the peak detecting circuit is reset to permit measuring the maximal angle of the T vector, if present. The maximal T Vector angle will always be determined from the magnitude of the T vector. When the peak of the T vector magnitude is detected, the instantaneous value of the vector angle is sensed by a second sample-and-hold amplifier which temporarily stores the sensed value of the T angle. In a preferred embodiment, the QRS angle and T angle are measured alternately and stored temporarily.

The stored voltage representing the maximal QRS vector angle is applied to the non-inverting input of an operational amplifier, and the stored voltage representing the maximal T vector angle is applied to the inverting input of the amplifier to obtain a difference output voltage which represents the differential QRS-T vector angle, as desired. (In the absence of a T vector, the output of the second sample-and-hold amplifier is zero volts, which represents a T vector angle of zero degrees. As a result, ventricular ectopi which lack the T vector are automatically measured and categorized for absolute QRS vector angle.)

The temporarily-stored sampled values of the QRS-T vector angle could be printed out or plotted at the end of each cycle of operation. This would result in a lengthy chain of data when a Holter recording of, for example, 24 hours' duration is analyzed. Such a lengthy chain of data would still require an unnecessarily large amount of time to analyze and study.

Accordingly, a classifying system is included in the present invention. In the classifying system, each successively stored value of QRS-T angle is tallied into one of a number of angular ranges. The cumulative tally in each of the pre-selected angular ranges is preserved on a counter specific to the range. The continually-updated counts on the counters can be continually displayed, printed out, or plotted.

Through the use of the present invention, in association with appropriate play-back apparatus, a 24-hour recording of two-channel ambulatory ECG signals can be quickly analyzed, and the arrhythmias present in the vectorcardiograph can be detected and classified with minimal operator intervention.

The apparatus of the present invention can also be used to measure and classify the vector angle at the peak of either the QRS complex or the T complex as desired, rather than to operate on their difference. This can be accomplished by a very simple modification to the preferred embodiment, which, when so modified, may be viewed as an alternative embodiment.

The novel features which are believed to characterize the invention, both as to organization and method of operation, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description only and not intended as a definition of the limits of the invention.

BRIEF DESCRIPTION OF THE DRAWINGS

FIG. 1 is a block diagram of a preferred embodiment of the present invention;

FIG. 2a is a schematic drawing of a practical digital one-of-N select logic used illustratively in a preferred embodiment of the present invention;

FIG. 2b is a table showing the states of the output lines for various states of the input lines of the digital one-of-N select logic circuit;

DESCRIPTION OF THE PREFERRED EMBODIMENT

Figure 3A:
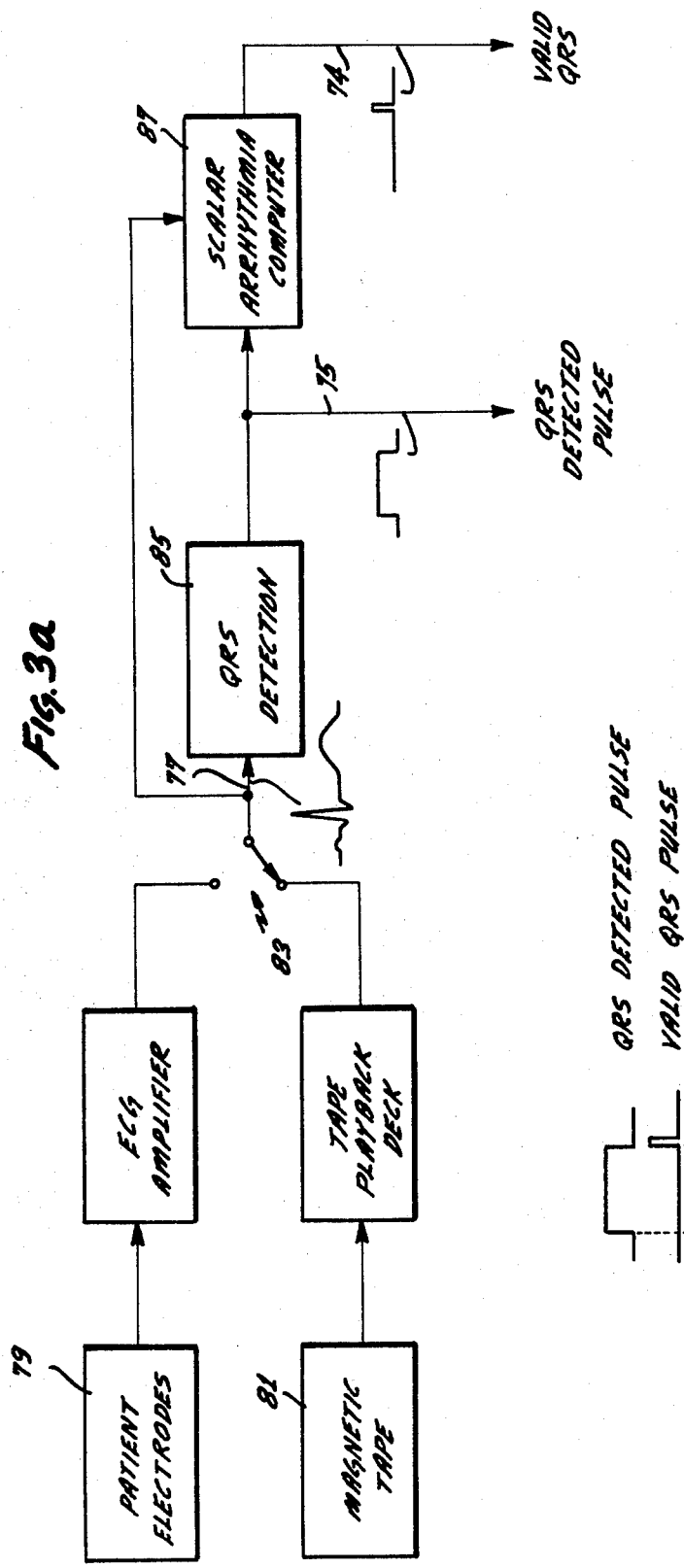
FIG. 3a is a block diagram showing the generation of the QRS Detected Pulse and the Valid QRS Pulse which are applied as inputs to the preferred embodiment of the present invention; and, FIG. 3b is a graph showing the ECG complex, the QRS Detected Pulse, and the Valid QRS Pulse versus time.

Turning now to the drawings, FIG. 1 is a block diagram of a preferred embodiment of the present invention, which also shows the best mode of practicing the invention.

The inputs to the apparatus include two approximately orthogonal channels of ECG signals shown at the left side of FIG. 1 and an optional scalar complex validation input shown at the upper right hand portion of the diagram of FIG. 1. The latter input will be discussed below. In the application entitled VECTORCARDIOGRAPHIC METHOD FOR AMBULATORY PATIENTS by Harold L. Kennedy, Ser. No. 786,252 filed Apr. 11, 1977, it was disclosed that medically significant vectorcardiograms can be produced using only two leads (4 electrodes) preferably a modified $V_5$ lead and a modified $V_1$ lead, as shown in that application. These leads can also be used as the channel 1 and channel 2 inputs to the apparatus of FIG. 1. In such event, the $V_5$ lead would preferably be used as the channel 1 input, because the peak of the R wave is more sharply defined in that lead generally. Leads other than $V_5$ and $V_1$ can also be used in the present invention, although the leads used would preferably be approximately orthogonal.

The channel 1 and channel 2 signals are the inputs to commercially-available rectangular-to-polar coordinate converter 12 of FIG. 1. The inputs are treated as the rectangular coordinates or components of the vector, and the device produces output signals representing the magnitude and the angle of the vector. These outputs are produced continually as long as the vector has any detectable magnitude, and the outputs are continually varying in time. A peak-determining circuit 14 is provided for use in first determining the apex of the QRS ventricular depolarization waveform and subsequently the apex of the T wave repolarization waveform. At the instant each apex occurs, the instantaneous values of each vector angle are sampled and held by the sample-and-hold amplifiers 16 and 17 of FIG. 1, the outputs of which are applied to differential amplifier 19 to obtain a voltage representing the differential QRS-T vector angle.

The peak-determining circuit may use either of two alternative inputs for determining the instant of occurrence of the apex of the ventricular depolarization (QRS) complex. A manual switch 21 is provided to permit enabling the selection of the alternative via electronic switch 18 at the proper time in the analysis sequence. In the preferred embodiment, the peak-determining circuit 14 monitors the magnitude of the vector present on line 20. The vectorcardiogram has different normal shapes for different people, and for the same person at difference times. In some cases, the magnitude M of the vector remains nearly constant over a moderate range of vector angle. In such cases, any errors made in determing the instant of occurrence of the peak magnitude will result in a seemingly disporportionately large error in the QRS vector angle. In this event, it is desirable to alter the position of the electronic switch 18 to the alternative position shown by the dashed lines, and in this alternative configuration, the apex of the ventricular depolarization waveform is determined from the peak of the R-wave of the signal on channel 1 and line 22, preferably the $V_5$ ECG lead.

Whichever signal is chosen, it is carried to the peak-determining circuit 14 on the line 24. The peak-determining circuit 14 determines the instant of occurrence of the peak of the input on the line 24 as follows. The input on the line 24 is applied to a voltage peak detector 26 which produces a continuous output on the line 30 equal to the maximum input voltage that has been applied to the line 24 within the current cycle of operation. The instantaneous value of the input signal on the line 28 is compared with the maximum signal on the line 30 in the voltage signal comparator 32. As long as the input to the voltage signal comparator 32 on the line 28 equals or exceeds the maximum signal on the line 30, there is no output from the voltage signal comparator 32. However, when the peak has been reached and the signal on the line 28 begins to decrease and falls below its maximum value on the line 30, the voltage signal comparator produces an output on the line 34. This output signal on the line 34 is produced approximately simultaneously with the occurrence of the peak of the signal on the line 24.

The peak-indicating signal on line 34 is applied to the logic AND gates 23 and 25 which select the proper sample-and-hold amplifier 16 or 17 that is to receive the resulting signal, depending upon whether the QRS or the T vector is being analyzed. When the QRS, or first portion of the signature is to be measured, the QRS detected pulse, described in connection with FIG. 3, is present, and the output AND gate 23 is enabled, which in turn is used to trigger the operation of the sample-and-hold amplifier 16, which stores the instantaneous signal on the line 36 at the time of occurrence of the triggering signal on the line 34.

At the termination of the QRS detected pulse, which is typically 200 ms after the commencement of the QRS complex, one-shot multivibrator 44 is triggered to produce a reset pulse on the line 46 to reset the voltage peak detector 26 back to an initial zeroed condition in preparation for measuring the T-wave magnitude.

From the above description, it can be seen that the operation of the peak-determining circuit 14 is the same, regardless whether the signal on the line 20 or the signal on the line 22 is used as an input. It is further pointed out that any variable could be selected for application to the line 36, to be sampled at the instant of occurrence of the apex of the ventricular depolarization complex; the angle of the vector is applied in the preferred embodiment of the invention because of its diagnostic significance.

The output of the sample-and-hold amplifier 16 is a constant signal on the line 48 which represents the sampled value of the vector angle. That value is maintained on the line 48 until replaced by the value obtained at the peak of the next occurring complex.

After one-shot 44 has reset the voltage peak detector 26, the detector will function as previously described to follow and hold the highest voltage amplitude that exists after it was reset. This will now be in the portion of the complex typically containing the T-wave, the peak magnitude of which generally occurs in the region of 250 to 650 milliseconds after the start of the QRS complex. Since the T-wave is typically the signal of greatest magnitude in this region, the voltage stored in the peak detector will be representative of it. At the instant the peak of the T-wave vector is detected, voltage comparator 32 will generate the signal for a second time. In this instance, however, AND gate 23 is inhibited by the absence of the QRS detected pulse. AND gate 25 is now enabled to receive the signal 34, because of the action of logic inverter 27. Sample-and-hold amplifier 17 is now triggered by the output of AND gate 25 to store the instantaneous signal on the line 36 at the time of occurrence of the triggering signal on the line 34. The stored output of amplifier 17 is applied to the inverting input of differential amplifier 19. Since line 48, containing the stored voltage representing the QRS vector angle, is applied to the non-inverting input of differential amplifier 19, the output voltage will represent the difference between the two angles, which is the desired differential QRS-T vector angle.

The output of the differential amplifier 19 is an essentially constant signal on the line 29 which represents the sampled value of the QRS-T vector angle. That value is maintained on the line 29 until after the next QRS detected pulse occurs.

The successive sampled values on the line 29 are applied to a plotter 50 to produce a visual display of the successive values versus time. The signal on the line 29 is the data input to the classifying circuit 52.

In the classifying circuit 52 of FIG. 1, a constant reference voltage is applied to a resistor divider network 54 to produce a set of reference signals on the lines 56 having various constant reference voltages in a preferred embodiment. Each of the lines 56 is an input to a separate voltage comparator circuit within the voltage comparator 58. The signal on the line 29 is applied to each of the individual voltage comparators comprising the voltage comparator circuit 58. These individual circuits sense the polarity of the difference between the signal on the line 29 and the reference voltage. The polarity sensed by each of the voltage comparators is represented by a binary signal on one of the lines 60.

Assuming that the reference voltages on the lines 56 are an increasing sequence of positive voltages, the polarity of the signals on the lines 60 will depend on the magnitude of the line 29. If the signal on line 29 is zero, each of the lines 60 will have a negative polarity. On the other hand, if the signal on the line 29 is extremely large—greater than any of the reference voltages—all of the lines 60 will carry a positive polarity. In the usual case, the signal on the line 29 will lie within the preselected range of reference voltages and therefore, typically, a first subset of the lines 60 will have a positive polarity, while the remaining lines 60 will have a negative polarity. This situation is illustrated in FIG. 2a where, by way of example, and not by way of limitation, six lines 60 are shown. FIG. 2a shows the digital one-of-N select logic circuit 62 of FIG. 1 in greater detail. The six AND gates 64 of FIG. 2a permit the vector angle on the line 29 to be classified into exactly one of seven angular ranges by way of illustration; in the preferred embodiment, 23 AND gates are used for greater resolution to classify the angle into one of 24 angular ranges, each 15 degrees wide. Additional resolution can be had by increasing the quantity of circuitry. Each of the AND gates 64 has three inputs. The lines 60 may be thought of as an electrical representation of the boundaries of the successive angular ranges. Based on the polarities on the lines 60 shown in FIG. 2a, it is seen that the vector angle lies within the range bounded by B and C. Activation of the AND gate W is based on the recognition that lines C and D have positive polarity and line B has negative polarity. The inverters 66 associated with each of the AND gates 64 reverse the polarity of the line corresponding to the boundary of the angular range which exceeds the vector angle.

FIG. 2b shows the state of each of the input lines A-F as the vector angle assumes ever-increasing values. Corresponding to each of these input states, the circuit 62 defines and produces a unique corresponding output state, as shown in FIG. 2b.

Thus, for each ECG signature, a single value of the QRS-T vector angle is sampled and is then classified into one of a number N of angular ranges, as indicated by the presence of the logic 1 on one of the output lines 68 of the digital one-of-N select logic circuit 62.

Returning to FIG. 1, the output lines 68 of the circuit 62 are applied to individual counters shown collectively as the counter circuit 70. After the start of each QRS complex has occurred, only one of the counters is incremented. The incrementing occurs when a clock pulse is applied to the counters via the line 72 which is connected to the clock input of each of the individual counters.

In the preferred embodiment, the clock pulse is not applied to the line 72 through the AND gate 42 unless a scalar complex validation input had occurred immediately previous on the line 74.

Flip-flop 31 provides a means for storing the occurrence of a scalar validation input pulse until it is needed after the T-wave vector angle has been measured. In the event flip-flop 31 was set by a signal on line 74, line 33 will rise to a logic 1 level. Since line 35 has no signal at this point, gate 42 will have no output. Upon the occurrence of another QRS detected pulse, the output of gate 42 will now go to a logic 1. This will always follow the occurrence of the T maximal vector. Thus, the counters 70 will be incremented by the presence of a logic 1 signal on line 72.

The use of the scalar complex validation input and flip-flop 31 of the preferred embodiment is optional in alternative embodiments. If used, the validation input is a signal derived from a scalar (as opposed to vector) arrhythmia detection system, as shown in FIG. 3a, to permit further rejection of artifacts such as are caused by muscle tension, electrode movement, electrical interference, etc., which might produce channel 1 and channel 2 inputs sufficiently large to be misinterpreted as ventricular depolarization complexes. Thus, the validation input assists the apparatus of the present invention in discriminating against false complexes. In the preferred embodiment, the AND gate 42 is activated by the leading edge of the pulse on the line 35 with the simultaneous presence of a logic 1 on the line 33. The leading edge of the pulse on the line 35 is coincident with the detection of the following QRS complex. However, this can alternately be accomplished at any time after the maximal T-wave vector was determined.

FIG. 3a is a block diagram showing how the QRS Detected Pulse input and the Validation input are derived for application to the preferred embodiment of the present invention shown in FIG. 1. These two inputs can be obtained from a commercially available ECG arrhythmia analysis device such as the Electrocardiographic Computer produced by Del Mar Avionics of Irvine, Calif., and described in U.S. Pat. No. 4,006,737 issued Feb. 8, 1977.

As shown in FIG. 3a, a scalar ECG signal on the line 77 can selectively be derived directly from electrodes 79 on a patient or from previously recorded signals on a magnetic tape 81, as determined by the position of the switch 83. The scalar ECG signal on the line 77 has the waveform indicated in the figure, and this signal is applied as an input to the QRS Detection circuit 85 which includes filtering, threshold and timing circuits to distinguish the QRS complex from the remainder of the ECG waveform and to produce on the line 75 the QRS Detected Pulse shown in the figure and applied as an input on the line 75 of FIG. 1.

The block diagram of FIG. 3 further includes the Scalar Arrhythmia Computer 87 which measures several scalar parameters of each ECG waveform, such as QRS width and amplitude, R-R prematurity, etc., and in so doing develops a logic signal on the line 74 which signifies that a valid QRS complex was received.

Figure 3B:
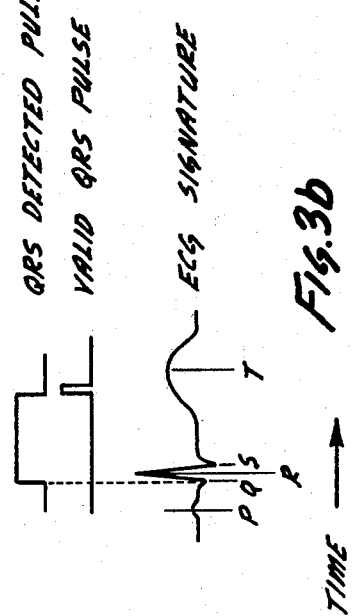

The QRS Detected Pulse on the line 75 is typically 200 milliseconds wide, commencing at the beginning of the QRS complex, as shown in FIG. 3b. The Valid QRS signal on the line 74 occurs at the end of the QRS Detected Pulse, by which time sufficient analysis has been performed by the Scalar Arrhythmia Computer 87 to determine whether the triggering signal was truly a QRS complex or was an artifact. A Valid QRS pulse will be developed only if a QRS complex is actually present.

The counters 70 are not reset at the end of each complex, and thus they accumulate the respective numbers of angles determined on successive signatures to have fallen into each of the angular ranges.

The accumulated data stored in the counters 70 is continually applied to the digital display 76 for visual observation, and is also applied to the printers 78 to produce a graphic record of the results of the analysis.

As pointed out above, the apparatus of the present invention is indifferent to whether the input signals on channel 1 and channel 2 are "live" signals obtained directly from ECG leads or are played back recorded signals. Further, the present invention is indifferent to the duration of the input signals, so long as the capacity of the counters 70 is not exceeded.

Further, with appropriate choice of circuit parameters, the circuit of FIG. 1 can be designed to operate with inputs obtained from the high speed playback of a magnetic tape recorded at real time speeds. Operation with high speed playback permits rapid analysis of recordings of relatively long duration. Prior to the invention of the present apparatus, the analysis could be performed only by observing the trace of the vector on the face of a cathode ray tube or by photographing the face of the cathode ray tube for each succeeding complex. If mere observation were used, the vector angles could not be determined with any precision, and lengthy samples could be tallied into various angular ranges only with great difficulty. On the other hand, photographing the face of the cathode ray tube for each successive vectorcardiogram and then measuring the vector angle on each photograph was a time-consuming and expensive proposition.

In contrast, the apparatus of the present invention senses and classifies the vector angles automatically, without intervention of an operator. The present invention permits a 24-hour sample to be analyzed in minutes, thereby multiplying the effectiveness of the medical staff.

It is recognized that if it is desired to measure and classify only one of the peak angles separately, rather than the difference between the peak angles, this can be accomplished simply by disconnecting one of the input leads to the differential operational amplifies of FIG. 1.

Numerous variations of the method in apparatus described above will be apparent to those skilled in the art. For example, the signals represented by voltages in the preferred embodiment could be represented by current or frequency in other embodiments. Such variations are included within the scope of the present invention which is limited only by the following claims.

What is claimed is:

1. Apparatus for use in analyzing successive ECG signatures in two-channel vector electrocardiographic signals for sensing the vector angle at the peak of the QRS complex and the vector angle at the peak of the T wave, for determining the difference between the vector angles, and for counting the number of times during a predetermined time interval the angular difference falls within predetermined angular limits, comprising:

peak-determining means responsive to an applied input signal for sensing the peak of the QRS complex and producing a first sampling signal when it occurs, and for sensing the peak of the T wave and producing a second sampling signal when it occurs;

a rectangular-to-polar coordinate converter responsive to the two-channel electrocardiographic signals to produce a magnitude signal and an angle signal;

sample-and-hold means connected to said peak-determining means, and connected to said rectangular-to-polar coordinate converter, and responsive to said first sampling signal to produce a first sampled angle signal equal to the value of the angle signal at the time of occurrence of the first sampling signal, and responsive to said second sampling signal to produce a second sampled angle signal equal to the value of the angle signal at the time of occurrence of the second sampling signal;

difference means connected to said sample-and-hold means for producing an output difference signal equal to the difference between the first sampled angle signal and the second sampled angle signal; and, classifying means connected to said difference means for counting the number of difference signals having amplitudes within a predetermined angular range.

2. The apparatus of claim 1 wherein the applied input signal to which said peak-determining means is responsive is the magnitude signal produced by said rectangular-to-polar coordinate converter.

3. The apparatus of claim 1 wherein the applied input signal to which said peak-determining means is responsive is a preselected one of the two vector electrocardiographic signals.

4. The apparatus of claim 1 further comprising validation means connected to said classifying means and responsive to an applied validating input signal to enable counting of a difference signal only when the applied validating input signal has a predetermined value.

5. The apparatus of claim 1 further comprising display means connected to said classifying means for displaying the counted numbers of difference signals.

6. The apparatus of claim 1 wherein said peak-determining means further comprises:

a peak detector responsive in each cycle of its operation to the applied input signal for continually producing an output signal equal to the greatest value of the applied input signal received during a cycle of operation, and responsive to an applied reset signal for terminating the cycle of operation; and, a signal comparator connected to said peak detector and responsive to the output of said peak detector and to the applied input signal for producing an output signal proportional to the difference between the applied input signal and the output of said peak detector.

7. The apparatus of claim 1 wherein said classifying means further comprises:

a source of N reference signals;

a signal comparator connected to said source of reference signals and to said difference means, and responsive to the output signal produced by said difference means to produce N output signals equal to the differences between the output of said difference means and each of the reference signals;

a one-of-N selection logic circuit connected to said signal comparator and having a number N of output lines and responsive to the output signals produced by said signal comparator for producing an output signal on one of the N output lines; and, a set of N counters, each connected to a different one of the N output lines of the one-of-N selector logic circuit and responsive to an applied clock input for incrementing each counter if an output signal is present on the output line to which the counter is connected.

8. The apparatus of claim 1 further comprising switch means connected to said peak determining means for alternatively selectively applying the magnitude signal and a predetermined one of the two vector electrocardiographic signals to said peak-determining means as the applied input signal.

9. Apparatus for counting the number of times during a predetermined time interval the vector angle at the peak of a chosen type of complex occurring within successive ECG signatures sensed in two-channel vector electrocardiographic signals occurs within predetermined angular limits, comprising:

peak-determining means responsive to an applied input signal for sensing the peak of each complex of the chosen type and for producing a sampling signal when the peak occurs;

a rectangular-to-polar coordinate converter responsive to the two electrocardiographic signals to produce a magnitude signal and an angle signal;

sample-and-hold means connected to said peak-determining means, and connected to said rectangular-to-polar coordinate converter, and responsive to the sampling signal to produce as an output a sampled angle signal equal to the value of the angle signal at the time of occurrence of the sampling signal; and, classifying means connected to said sample-and-hold means for counting the number of sampled angle signals whose amplitudes fall within a predetermined angular range.

10. The apparatus of claim 9 wherein the applied input signal to which said peak-determining means is responsive is the magnitude signal produced by said rectangular-to-polar coordinate converter.

11. The apparatus of claim 9 wherein the applied input signal to which said peak-determining means is responsive is a preselected one of the two vector electrocardiographic signals.

12. The apparatus of claim 9 further comprising validation means connected to said classifying means and responsive to an applied validating input signal to enable counting of a sampled angle signal only when the applied validating input signal has a predetermined value.

13. The apparatus of claim 9 further comprising display means connected to said classifying means for displaying the counted numbers of sampled angle signals.

14. The apparatus of claim 9 wherein said peak determining means further comprises:

a peak detector responsive in each cycle of its operation to the applied input signal for producing an output signal equal to the greatest value of the applied input signal received during a cycle of operation, and responsive to an applied reset signal for terminating the cycle of operation; and, a signal comparator connected to said peak detector and responsive to the output of said peak detector and to the applied input signal for producing an output signal equal to the difference between the applied input signal and the output of said peak detector.

15. The apparatus of claim 9 wherein said classifying means further comprises:

a source of N reference signals;

a signal comparator connected to said source of reference signals and to said sample-and-hold means, and responsive to the output signal produced by said sample-and-hold means to produce N output signals equal to the differences between the output of said sample-and-hold means and each of the reference signals;

a one-of-N selection logic circuit connected to said signal comparator and having a number N of output lines and responsive to the output signals produced by said signal comparator for producing an output signal on one of the N output lines; and, a set of N counters, each connected to a different one of the N output lines of the one-of-N selector logic circuit and responsive to an applied clock input for incrementing each counter if an output signal is present on the output line to which the counter is connected.

16. The apparatus of claim 9 further comprising switch means connected to said peak-determining means for alternatively selectively applying the magnitude signal and a predetermined one of the two vector electrocardiographic signals to said peak-determining means as the applied input signal.

17. A method for determining the number of times during a predetermined time interval the difference between the vector angles at the peaks of successive QRS and T complexes within successive ECG signatures in two-channel vector electrocardiographic signals occurs within predetermined angular limits, comprising the steps of:

(a) converting the two-channel vector electrocardiographic signals to polar form including a magnitude signal and an angle signal;

(b) producing a sampling signal at the instant when the peak of a complex occurs;

(c) sampling the angle signal when the sampling signal is produced;

(d) repeating Steps (a)–(c) for the next complex within the signature;

(e) subtracting the successive sampled angle signals obtained in Steps (c) and (d) to obtain a difference signal;

(f) comparing the difference signal with a series of reference signals to determine which angular range the difference signal falls into;

(g) incrementing, by one count, a counter associated with the angular range into which the difference signal falls; and, (h) repeating Steps (a) through (g) for each successive signature which occurs within the predetermined time interval.

18. The method of claim 17 further comprising the step of determining between Step (a) and Step (b) the instant at which the peak of a complex occurs as being the instant when the magnitude of the vector has attained a maximum value.

19. The method of claim 17 further comprising the step of determining between Step (a) and Step (b) the instant at which the peak of a complex occurs as being the instant when a preselected one of the two electrocardiographic signals has attained a maximum value.

20. A method for determining the number of times during a predetermined time interval the vector angle at the peak of a chosen type of complex occurring within successive ECG signatures sensed in two-channel vector electrocardiographic signals occurs within predetermined angular limits, comprising the steps of:

(a) converting the two-channel vector electrocardiographic signals to polar form including a magnitude signal and an angle signal;

(b) producing a sampling signal at the instant when the peak of a complex occurs;

(c) sampling the angle signal when the sampling signal is produced;

(d) comparing the sampled angle signal with a series of reference signals to determine which angular range the sampled angle signal falls into;
(e) incrementing, by one count, a counter associated with the angular range into which the sampled angle falls; and,
(f) repeating Steps (a) through (e) for each successive ECG signature which occurs within the predetermined time interval.

21. The method of claim 20 further comprising the step of determining between Step (a) and Step (b) the instant at which the peak of a complex occurs as being the instant when the magnitude of the vector has attained a maximum value.

22. The method of claim 20 further comprising the step of determining between Step (a) and Step (b) the instant at which the peak of a complex occurs as being the instant when a preselected one of the two electrocardiographic signals has attained a maximum value.

* * * * *